(12) United States Patent
Bathe et al.

(10) Patent No.: US 6,762,300 B2
(45) Date of Patent: Jul. 13, 2004

(54) METHOD FOR PRODUCING 5-(1-PIPERAZINYL)-BENZOFURAN-2-CARBOXAMIDE BY TRANSITION METAL-CATALYZED AMINATION

(75) Inventors: Andreas Bathe, Darmstadt (DE); Steffen Emmert, Weiterstadt (DE); Bernd Helfert, Ober-Ramstadt (DE); Henning Boettcher, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/148,567
(22) PCT Filed: Nov. 29, 2000
(86) PCT No.: PCT/EP00/11980
§ 371 (c)(1), (2), (4) Date: Oct. 10, 2002
(87) PCT Pub. No.: WO01/40219
PCT Pub. Date: Jun. 7, 2001

(65) Prior Publication Data
US 2003/0125558 A1 Jul. 3, 2003

(30) Foreign Application Priority Data
Dec. 4, 1999 (DE) .......................................... 199 58 496

(51) Int. Cl.⁷ ................... C07D 405/10; C07D 295/112; C07D 295/185

(52) U.S. Cl. ....................... 544/376; 544/374; 544/389; 544/392; 544/395
(58) Field of Search ................................. 544/376, 389, 544/392, 395, 374

(56) References Cited

U.S. PATENT DOCUMENTS 4,210,646 A * 7/1980 Janssen .................. 514/255.03
4,814,262 A * 3/1989 Sugita et al. ............... 430/551

FOREIGN PATENT DOCUMENTS

| EP | 738722 | * 10/1996 |
| EP | 802173 | * 10/1997 |
| EP | 846676 | * 6/1998 |

OTHER PUBLICATIONS

Nishiyama et al. Tet. Lett. 39,p.617–620 (1998).*

* cited by examiner

*Primary Examiner*—Emily Bernhardt
(74) *Attorney, Agent, or Firm*—Millen, White, Zelano & Branigan, P.C.

(57) ABSTRACT

Process for the preparation of 5-(1-piperazinyl)benzofuran-2-carboxamide in which, as intermediate step, 5-bromosalicylaldehyde or one of its derivatives is reacted in a transition metal-catalysed amination with $R^2$-piperazine, in which $R^2$ is as defined in claim 1.

16 Claims, No Drawings

METHOD FOR PRODUCING 5-(1-PIPERAZINYL)-BENZOFURAN-2-CARBOXAMIDE BY TRANSITION METAL-CATALYZED AMINATION

The invention relates to a process for the preparation of 5-(1-piperazinyl)benzofuran-2-carboxamide, characterized in that a) 5-bromosalicylaldehyde is reacted in a one-pot reaction firstly with a compound of the formula I

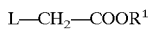

in which

L is Cl, Br, I or a reactively esterified OH group, and
$R^1$ is alkyl having 1–6 carbon atoms or benzyl,
and subsequently with formamide to give 5-L-benzofuran-2-carboxamide (II), in which L is Cl, Br, I or a reactively esterified OH group,
(II) is then reacted in a transition metal-catalysed amination with $R^2$-piperazine, in which $R^2$ is H or an amino protecting group, to give the compound of the formula III

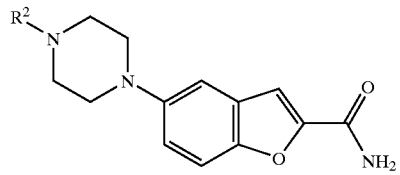

in which $R^2$ is H or an amino protecting group,
and subsequently, if $R^2 \neq H$, $R^2$ is cleaved off, or b) a compound of the formula IV

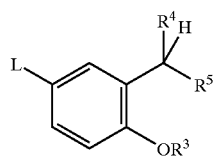

in which

L is Cl, Br, I or a reactively esterified OH group,
$R^3$ is H or $CH_2R^6$,
$R^4$ and $R^5$ are each, independently of one another, $OR^7$, $OR^8$, $SR^7$ or $SR^8$,
$R^4$ and $R^5$ together are alternatively carbonyl, =S, =N—C($R^7$)$_2$, =N—C($R^8$)$_2$, =N—OH, =N—$OR^7$, =N—N[($R^7$)$_2$], =N—N[($R^8$)$_2$] or —O—(CH$_2$)$_n$—O—,
$R^6$ is CN, COOH, $COOR^7$ or $CONH_2$,
$R^7$ is alkyl having 1–6 carbon atoms,
$R^8$ is phenyl which is unsubstituted or mono- or disubstituted by $R^7$, $OR^7$, $SR^7$ or Hal,
n is 2 or 3,
is reacted in a transition metal-catalysed amination with $R^2$-piperazine, in which $R^2$ is H or an amino protecting group, to give a compound of the formula V

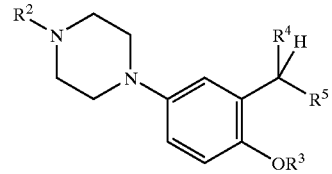

in which $R^2$ is H or an amino protecting group,
$R^3$ is H or $CH_2R^6$,
$R^4$ and $R^5$ are each, independently of one another, $OR^7$, $OR^8$, $SR^7$ or $SR^8$,
$R^4$ and $R^5$ together are alternatively carbonyl, =S, =N—C($R^7$)$_2$, =N—C($R^8$)$_2$, =N—OH, =N—$OR^7$, =N—N[($R^7$)$_2$], =N—N[($R^8$)$_2$] or —O—(CH$_2$)$_n$—O—,
$R^6$ is CN, COOH, $COOR^7$ or $CONH_2$,
$R^7$ is alkyl having 1–6 carbon atoms,
$R^8$ is phenyl which is unsubstituted or mono- or disubstituted by $R^7$, $OR^7$, $SR^7$ or Hal,
n is 2 or 3,
which is subsequently reacted in a one-pot reaction firstly with a compound of the formula I

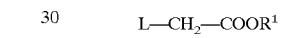

in which

L is Cl, Br, I or a reactively esterified OH group, and
$R^1$ is alkyl having 1–6 carbon atoms or benzyl,
and subsequently with formamide to give a compound of the formula III

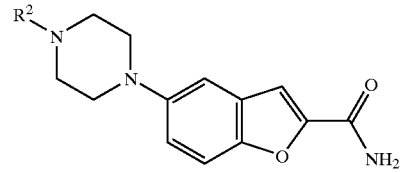

in which $R^2$ is H or an amino protecting group,
and subsequently, if $R^2 \neq H$, $R^2$ is cleaved off, or c) a compound of the formula V
in which
$R^2$ is an amino protecting group,
$R^3$ is H or $CH_2R^6$,
$R^4$ and $R^5$ are each, independently of one another, $OR^7$, $OR^8$, $SR^7$ or $SR^8$,
$R^4$ and $R^5$ together are alternatively carbonyl, =S, =N—C($R^7$)$_2$, =N—C($R^8$)$_2$, =N—OH, =N—$OR^7$, =N—N[($R^7$)$_2$], =N—N[($R^8$)$_2$] or —O—(CH$_2$)$_n$—O—,
$R^6$ is CN, COOH, $COOR^7$ or $CONH_2$,
$R^7$ is alkyl having 1–6 carbon atoms,
$R^8$ is phenyl which is unsubstituted or mono- or disubstituted by $R^7$, $OR^7$, $SR^7$ or Hal,
n is 2 or 3,
is reacted with chloroacetamide to give a compound of the formula III in which R² is an amino protecting group,
and R² is subsequently cleaved off,
and/or in that 5-(1-piperazinyl)benzofuran-2-carboxamide is converted into one of its acid-addition salts by treatment with an acid.

The invention also relates to the compounds of the formula V

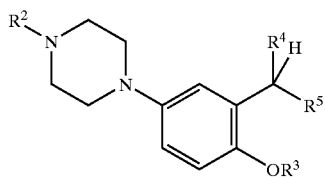

in which
R² is H or an amino protecting group,
R³ is H or CH₂R⁶,
R⁴ and R⁵ are each, independently of one another, OR⁷, OR⁸, SR⁷ or SR⁸,
R⁴ and R⁵ together are alternatively carbonyl, =S, =N—C(R⁷)₂, =N—C(R⁸)₂, =N—OH, =N—OR⁷, =N—N[(R⁷)₂], =N—N[(R⁸)₂] or —O—(CH₂)ₙ—O—,
R⁶ is CN, COOH, COOR⁷ or CONH₂,
R⁷ is alkyl having 1–6 carbon atoms,
R⁸ is phenyl which is unsubstituted or mono- or disubstituted by R⁷, OR⁷, SR⁷ or Hal,
n is 2 or 3,
and salts and solvates thereof.

5-(1-piperazinyl)benzofuran-2-carboxamide is an important intermediate for pharmaceutical active ingredients. This is described, for example, in DE 19730989, WO 9857953, EP 738722, EP 736525, DE 4414113, DE 4333254 or DE 4101686.

Benzofuran derivatives as precursors are also described, for example, in DE 19514567.

Processes are known for the preparation of heterocyclic aromatic amines or arylamines, for example from EP 0 802 173, in which a transition-metal catalyst is used.

General amination reactions are described in a review article by J. F. Martinez in Angew, Ch. Int. 37, 2046–2062. Other processes for the preparation of tertiary arylamines using a catalyst composed of a trialkylphosphine and palladium are disclosed in JP 10-310561 (Kokai application), Appl. No. 9-119477 or JP 11-80346 (Kokai application), Appl. No. 9-245218.

A process for the preparation of arylamines with transition-metal catalysis has been described by S. L. Buchwald et al. in U.S. Pat. No. 5,576,460. Another process for the preparation of aromatic amines from chlorinated aromatic compounds in the presence of a palladium catalyst is described in EP 0 846 676, by J. F. Hartwig et al. in J. Org. Chem. 1999, pp. 5575–5580, or S. L. Buchwald et al. in J.A.C.S. 1999, 121, 9550–9561.

In Tetrahedron Letters 39 (1998) 617–620, M. Nishiyama describes the synthesis of N-arylpiperazines from aryl halides and piperazine with transition-metal catalysis.

Surprisingly, studies in the course of the synthesis of medicaments which are described, for example, in DE 43 33 254 (EP 0 648 767) have shown that 5-(1-piperazinyl) benzofuran-2-carboxamide can be obtained in at least comparable or higher overall yield compared with the prior art, crucial advantages which may be mentioned here being the fact that the reaction is simple to carry out and product isolation is consequently simple.

Another consequence of this is the low solvent and energy consumption.

If L in the compounds of the formulae I, II or IV is a reactively esterified OH group, this is preferably alkylsulfonyloxy having 1–6 carbon atoms (preferably methylsulfonyloxy or trifluoromethylsulfonyloxy), arylsulfonyloxy having 6–10 carbon atoms (preferably phenyl- or p-tolylsulfonyloxy, furthermore also 2-napthalenesulfonyloxy) or alternatively fluorosulfonyloxy.

R¹ is alkyl or benzyl. Alkyl here has 1, 2, 3, 4, 5 or 6 carbon atoms, preferably 1, 2, 3 or 4 carbon atoms, particularly preferably, for example, methyl or ethyl, furthermore propyl, isopropyl, furthermore also butyl, isobutyl, sec-butyl or tert-butyl.

In the compounds of the formula I, L is preferably Cl, furthermore also Br.

R² is H or an amino protecting group. R² is particularly preferably an amino protecting group.

The term "amino protecting group" is known in general terms and refers to groups which are suitable for protecting (blocking) an amino group against chemical reactions, but which are easy to remove after the desired chemical reaction has been carried out elsewhere in the molecule. Typical such groups are, in particular, unsubstituted acyl, aryl, aralkoxymethyl or aralkyl groups. Since the amino protecting groups are removed after the desired reaction (or reaction sequence), their type and size are furthermore not crucial; however, preference is given to those having 1–20, in particular 1–8, carbon atoms. The term "acyl group" in connection with the present process and the present compounds should be understood in the broadest sense. It covers acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of acyl groups of this type are alkanoyl, such as acetyl, propionyl, butyryl; aralkanoyl, such as phenylacetyl; aroyl, such as, benzoyl or tolyl; aryloxyalkanoyl, such as phenoxyacetyl; alkoxycarbonyl, such as methoxycarbonyl, ethoxycarbonyl, 2,2,2-trichloroethoxycarbonyl, BOC (tert-butoxycarbonyl), 2-iodoethoxycarbonyl; aralkyloxycarbonyl, such as CBZ (carbobenzoxycarbonyl), also referred to as "Z"), 4-methoxybenzyloxycarbonyl, FMOC (9-fluorenylmethoxycarbonyl); arylsulfonyl, such as Mtr (4-methoxy-2,3,6-trimethylphenylsulfonyl).

R² is very particularly preferably benzyl or BOC.

An amino protecting group can be removed from a compound of the formula III—depending on the protecting group used—using, for example, strong acids, advantageously using TFA (trifluoroacetic acid) or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic solvents, for example carboxylic acids, such as acetic acid, ethers, such as tetrahydrofuran or dioxane, amides, such as dimethylformamide, halogenated hydrocarbons, such as dichloromethane, furthermore also alcohols, such as methanol, ethanol or isopropanol, and water. Also suitable are mixtures of the above-mentioned solvents. TFA is preferably used in excess without addition of a further solvent, and perchloric acid is preferably used in the form of a mixture of acetic acid and 70% perchloric acid in the ratio 9:1. The reaction temperatures are advantageously between about 0 and about 50°, preferably between 15 and 30°. The BOC group is preferably cleaved off using TFA in dichloromethane or using approximately 3 to 5N hydrochloric acid in dioxane at 15–30°.

Protecting groups which can be removed hydrogenolytically (for example CBZ or benzyl) can be cleaved off, for example, by treatment with hydrogen in the presence of a catalyst (for example a noble-metal catalyst, such as palladium, advantageously on a support, such as carbon). Suitable solvents here are those mentioned above, in particular, for example, alcohols, such as methanol or ethanol, or amides, such as DMF. The hydrogenolysis is generally carried out at temperatures between about 0 and 100° and pressures between about 1 and 200 bar, preferably at 20–30° and 1–10 bar.

$R^3$ is preferably H.

$R^3$ $R^4$ and $R^5$ are preferably methoxy, ethoxy, propoxy or phenoxy.

$R^4$ and $R^5$ are in particular together carbonyl.

In the compounds of the formula IV, Hal is preferably Br.

The compounds of the formula IV and V can also be in dimeric form which can be cleaved back to the corresponding salicylaldehydes, in which L and $R^2$ have the meanings indicated:

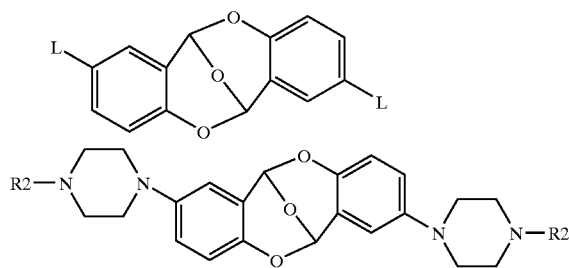

$R^7$ is alkyl. Alkyl here has 1, 2, 3, 4, 5 or 6 carbon atoms, preferably 1, 2, 3 or 4 carbon atoms, particular preference being given, for example, to methyl or ethyl, furthermore propyl, isopropyl, furthermore also butyl, isobutyl, sec-butyl or tert-butyl.

In the compounds of the formulae IV and V,
=N—C($R^7$)$_2$ is preferably =N—C(CH$_3$)$_2$,
=N—C($R^8$)$_2$ is preferably =N—C(phenyl)$_2$,
=N—O$R^7$ is preferably =N—OCH$_3$,
=N—N[($R^7$)$_2$] is preferably =N—N[(CH$_3$)$_2$],
=N—N[($R^8$)$_2$] is preferably =N—N[(phenyl)$_2$].

The compounds of the formulae I and IV are either known or are otherwise prepared by methods known per se, as described in the literature (for example in the standard works, such as Houben-Weyl, Methoden der organischen Chemie [Methods of Organic Chemistry], Georg-Thieme Verlag, Stuttgart), to be precise under reaction conditions which are known and suitable for said reactions. Use can also be made here of variants which are known per se, but are not mentioned here in greater detail.

Process Variant a)

The reaction of 5-bromosalicylaldehyde with a compound of the formula I and subsequently with formamide is carried out as a one-pot reaction in a suitable inert solvent with addition of a base.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane, ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; nitriles, such as acetonitrile; sulfoxides, such as dimethyl sulfoxide (DMSO); carbon disulfide; nitro compounds, such as nitromethane or nitrobenzene; optionally also mixtures of said solvents with one another.

The reaction time, depending on the conditions used, is between a few minutes and 14 days, and the reaction temperature is between about 0° and 150°, preferably between 60° and 120°.

The reaction time is very particularly preferably between 4 and 20 hours and the temperature between 90 and 115°.

Suitable bases are compounds such as, for example, Na, K or Cs carbonate.

A one-pot reaction is subsequently carried out with formamide, preferably in the presence of an organic base, preferably an alkali metal alkoxide, such as, for example, Na tert-butoxide, and its corresponding alcohol, to give 5-Hal-benzofuran-2-carboxamide (II). In (II), Hal is preferably Br.

The reaction is preferably carried out at from 0 to 60°.

Other processes to give (II) are described, for example, in Bull. Soc. Chim. Fr., 1971; 4329, and by O. Dann et al. in Justus Liebigs Ann. Chem. 1975; 160–194. The one-pot reaction described above proceeds in better yield than said reactions.

The reaction of (II) with $R^2$-piperazine to give the compound of the formula III is carried out in a suitable inert solvent, a base and in the presence of a transition-metal catalyst.

Transition metals which can be employed include PdCl$_2$ or Pd(OAc)$_2$ or other Pd$^{2+}$ derivatives, which are pre-reduced, for example using NaBH$_4$ or phosphines (the step can be omitted in the case of an excess of ligand R$_3$P) or Pd(0) species, such as, for example, Pd(DBA)$_2$ or Pd$_2$(DBA)$_3$ (DBA=dibenzylideneacetone)

To this range of Pd complexes can be added corresponding ligand complexes of nickel or copper.

Furthermore, ligands which can be employed are N,N-diarylimidazolium salts analogously to J. Huang et al., Org. Lett. 1, 1999, 1307–1309.

The phosphine or aza/phosphine ligands employed include
tris-ortho-tolylphosphine
tricyclohexylphosphine
1-(2-diphenylphosphino-1-naphthyl)isoquinoline (QUINAP)
1,8-bis(dimethylamino)naphthalene
Phe$_2$P—CH$_2$—PPhe$_2$
in particular also P(tert-butyl)$_3$=P(t-Bu)$_3$
1,1'-bis(diphenylphosphano)ferrocene (DPPF as complex DPPFxPdCl$_2$)
2,2'-bis(diphenylphosphino)-1,1'-binaphthyl (=BINAP)
(S)-dibutphos=1-(2-di-tert-butylphosphanylphenyl) ethyldimethylamine
1-(N,N-dimethylamino)-1'-(dicyclohexylphosphino) biphenyl
1-(di-t-butylphosphino)biphenyl
1,1'-bis(di-t-butylphosphino)biphenyl
(t-Bu)$_2$P—(CH$_2$)$_n$—P(t-Bu)$_2$ n=1,2,3
(t-Bu)$_2$P—(CH$_2$)$_m$—X—(CH$_2$)$_n$—P(t-Bu)$_2$ m,n=1, 2, 3; X=O, . . .
or alternatively
DB$^t$PF=1,1'-bis(di-tert-butylphosphino)ferrocene.

Examples of suitable solvents are hydrocarbons, such as benzene, toluene, xylene; chlorinated hydrocarbons, such as, for example, dichloromethane; ketones, such as acetone, butanone; ethers, such as tetrahydrofuran (THF) or dioxane; nitriles, such as acetonitrile, optionally also mixtures of these solvents with one another.

The reaction time, depending on the conditions used, is between a few minutes and 14 days, and the reaction temperature is between 0° and 180°, normally between 30° and 130°.

Examples of suitable bases are alkali metal alkoxides, such as, for example, Na tert-butoxide.

Process Variant b)

The reaction of compounds of the formula IV with $R^2$-piperazine is carried out under conditions as described under variant a).

$R^4$ and $R^5$ are optionally converted into a carbonyl group. The subsequent one-pot reaction of the compound of the formula V with the compound of the formula I and subsequently with formamide is likewise carried out under conditions as described above. The elimination of $R^2$, if $R^2 \neq H$, is also carried out under the conditions described.

A base of the formula I or of the formula V can be converted into the associated acid-addition salt by means of an acid, for example by reaction of equivalent amounts of the base and the acid in an inert solvent, such as ethanol, followed by evaporation. Particularly suitable acids for this reaction are those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acids. Salts with physiologically unacceptable acids, for example picrates, can be used for the isolation and/or purification of the compounds of the formula I.

Above and below, all temperatures are given in ° C. In the examples below, "conventional work-up" means that water is added if necessary, the pH is adjusted to between 2 and 10 if necessary, depending on the constitution of the end product, the product is extracted with ethyl acetate or dichloromethane, the phases are separated, the organic phase is dried over sodium sulfate and evaporated, and the product is purified by chromatography on silica gel and/or by crystallization.

EXAMPLE 1

1) Synthesis of 5-bromobenzofuran-2-carboxamide

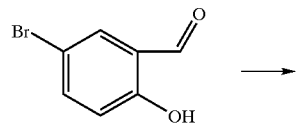

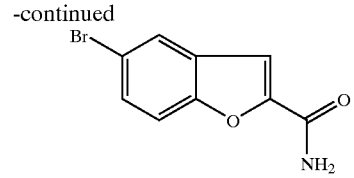

Performance of the reaction with ethyl bromoacetate: 200 g of 5-bromo-2-hydroxybenzaldehyde are dissolved in 2000 ml of NMP with stirring, and 144 g of potassium carbonate and 175 g of ethyl bromoacetate are added. The mixture is stirred at 105° under nitrogen for 15 hours. The resultant orange solution dotted with crystals is cooled to 25°, 135 g of formamide are added, and the mixture is stirred for a further 30 minutes. 557 ml of sodium methoxide (30% in MeOH) are then allowed to run in over the course of 15 minutes without cooling. After 3 hours, a brownish solution dotted with crystals is present. It is poured into 6 litres of demineralized water (10°), and the mixture is stirred for a further 30 minutes. The crystals are filtered off with suction, washed with 1 litre of demineralized water, re-suspended in 4 litres of demineralized water, filtered off with suction and re-washed with 1 litre of demineralized water. The crystals are dried overnight to constant weight under reduced pressure at 60° C. (product weight: 113 g of pale beige crystals; m.p. 210–213°; CAS 35351-21-4).

The physical and spectroscopic data correspond to the data published in: Rene; Royer; BSCFAS; Bull. Soc. Chim. Fr.; 1971; 4329, and Dann, O. et al.; JLACBF; Justus Liebigs Ann. Chem.; GE; 1975; 160–194.

5-Chlorobenzofuran-2-carboxamide (m.p. 200–202°), 5-fluorobenzofuran-2-carboxamide and 5-iodobenzofuran-2-carboxamide can be obtained in comparable yields using the same method.

2) Synthesis of 5-(4-benzyl-1-piperazinyl)benzofuran-2-carboxamide by transition metal-catalysed amination of 5-bromobenzofuran-2-carboxamide using benzylpiperazine

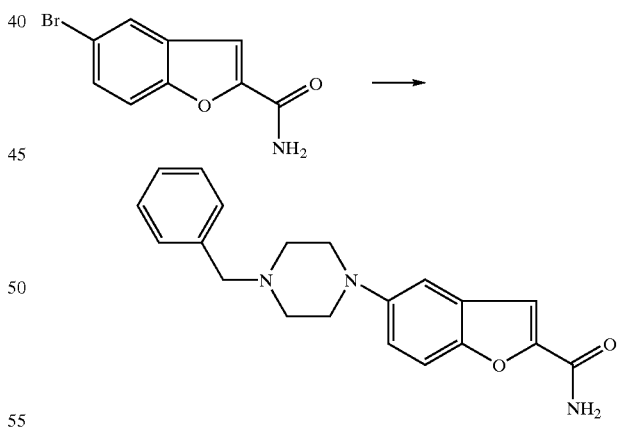

Illustrative performance using the catalyst system Pd(OAc)$_2$/P(t-Bu)$_3$:

0.30 g of P(t-Bu)$_3$, 4.5 g of 5-bromobenzofuran-2-carboxamide, 4.9 g of benzylpiperazine and 5.0 g of Na t-OBu are added to a suspension of 0.085 g of Pd(II) acetate in 150 ml of xylene after the latter has been stirred for 15 minutes, and the mixture is warmed at 125° C. for 12–18 hours under the protective gas nitrogen. After cooling, the mixture is added to 500 ml of 2N hydrochloric acid, and the aqueous phase is extracted 3 times with 200 ml of ethyl acetate. The aqueous phase is adjusted to pH 10 using aqueous NaOH (20%) with pH and temperature monitoring (20–25° C.), and the 5-(4-benzyl-1-piperazinyl)benzofuran-2-carboxamide produced as a solid is filtered off and crystallized, for example, from ethanol/water (product weight: 4.0 g/64%/m.p. 277–279°).

3) Synthesis of 5-(1-piperazinyl)benzofuran-2-carboxamide from 5-(4-benzyl-1-piperazinyl)benzofuran-2-carboxamide

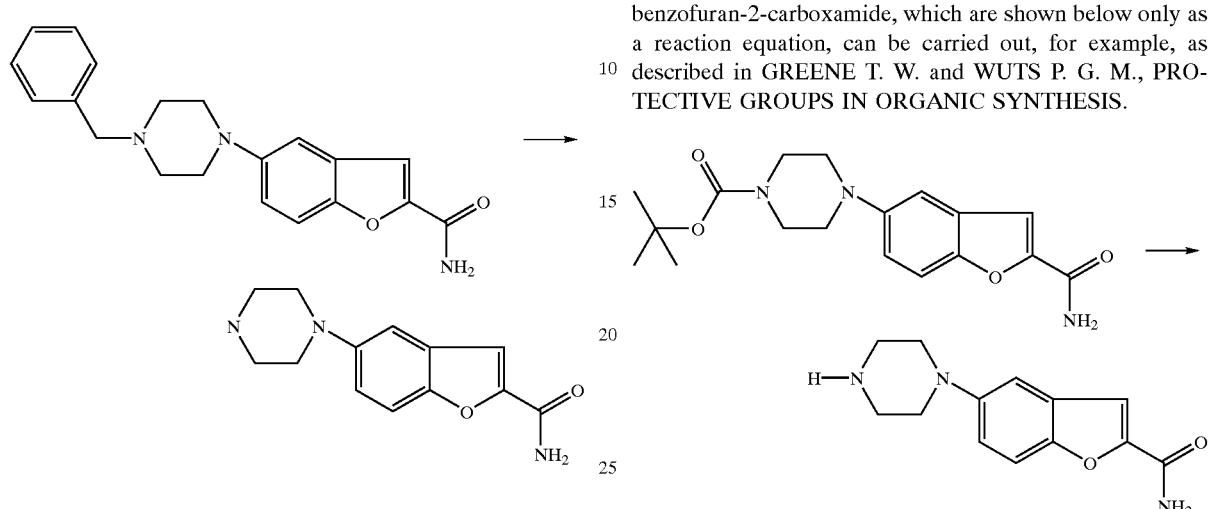

Hydrogenolysis procedure:

5.0 g of 5-(4-benzyl-1-piperazinyl)benzofuran-2-carboxamide are added to 300 ml of ethanol, and, after 9 g of palladium on activated carbon (5%) and 5 g of HOAc (100%) have been added, the product is debenzylated to completion at 20–30° C. using hydrogen. After filtration and removal of the solvent under reduced pressure and crystallization from alcohol or water and drying at 60° C. under reduced pressure, the product can be isolated (3.1 g/85%/ m.p. 252–255°, spectroscopically identical with the material prepared by previous methods; described, inter alia, in DE 4101686/laid open Jul. 23, 1992; DE 4333254/laid open Apr. 6, 1995; EP 0648767/published Apr. 19, 1995; EP 0738722/published Oct. 23, 1996).

EXAMPLE 2

1) Synthesis of 5-(4-tert-butoxycarbonyl-1-piperazinyl)benzofuran-2-carboxamide from 5-bromobenzofuran-2-carboxamide

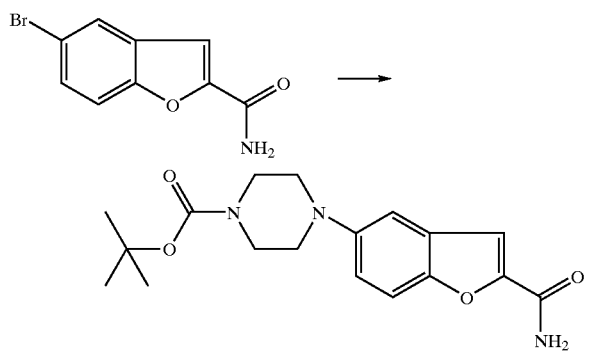

0.9 g of 5-bromobenzofuran-2-carboxamide, 1.1 g of BOC-piperazine and 1.45 g of Na t-OBu are added to a suspension of 0.06 g of Pd(DBA)$_2$ and 0.25 g of P(t-Bu)$_3$ in 40 ml of diethylene glycol dimethyl ether, and the mixture is warmed at 120–130° C. for 16 hours under a protective gas. After cooling, the mixture is added to water, and the organic phase is diluted with 100 ml of MTBE and washed with 3×50 ml of water. The solvent is evaporated, and the product formed as a solid is filtered off and purified by crystallization from ethanol (product weight: 0.7 g/55%/ m.p. 210–213°).

The subsequent removal of the BOC protecting group using hydrochloric acid and formation of 5-(1-piperazinyl)benzofuran-2-carboxamide, which are shown below only as a reaction equation, can be carried out, for example, as described in GREENE T. W. and WUTS P. G. M., PROTECTIVE GROUPS IN ORGANIC SYNTHESIS.

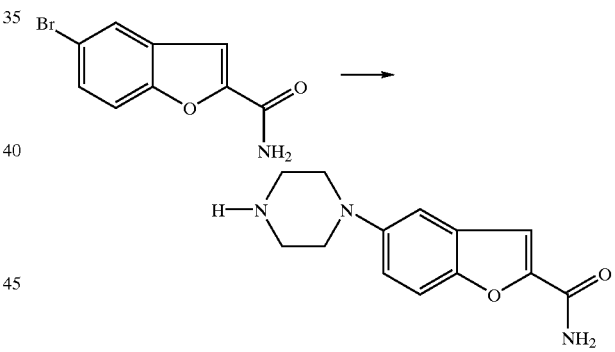

EXAMPLE 3

Synthesis of 5-(1-piperazinyl)benzofuran-2-carboxamide from 5-bromobenzofuran-2-carboxamide 0.9 g of 5-bromobenzofuran-2-carboxamide, 0.97 g of piperazine and 2.20 g of Na t-OBu are added to a suspension of 0.06 g of Pd(DBA)$_2$ and 0.07 g of 1-(N,N-dimethylamino)-1'-(dicyclohexylphosphino)biphenyl in 50 ml of toluene, and the mixture is warmed at 120–130° for 16 hours under a protective gas. After cooling, the reaction mixture is added to a mixture of 50 ml of water and 10 ml of 37% hydrochloric acid, 100 ml of ethyl acetate are added, and the mixture is stirred for 20 minutes. A little undissolved product is then removed, and the organic phase is separated off. The aqueous phase is washed again by shaking with 50 ml of ethyl acetate and freed from solvent residues under reduced pressure, clarified using charcoal and filtered. The product is precipitated in crystalline form from the filtrate at 20–22° using 20–25 ml of 32% sodium hydroxide solution. The product is filtered off and dried (product weight: 0.65 g/70% /m.p. 252–255°).

EXAMPLE 4

1) Synthesis of 5-(4-benzylpiperazin-1-yl)-2-hydroxybenzaldehyde

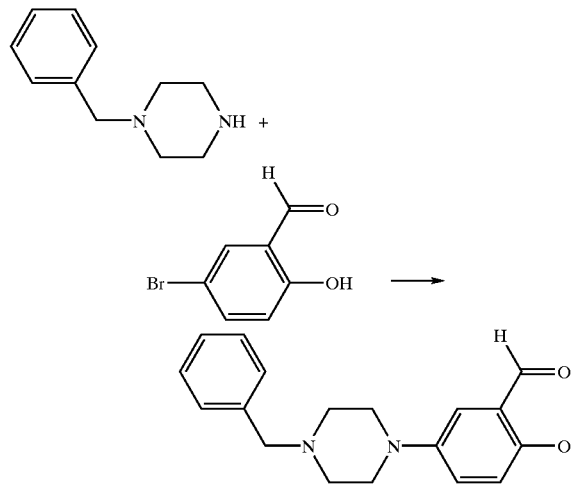

0.6 g of bis(dibenzylideneacetone)palladium and 0.16 g of tri-tert-butylphosphine are added under nitrogen to 200 ml of toluene, and the resultant dark-red solution is stirred at 20° for 20 minutes. 10 g of 5-bromo-2-hydroxybenzaldehyde, 9.7 g of 1-benzylpiperazine and 7.2 g of sodium tert-butoxide are then added. The mixture is stirred at 60° for 24 hours and cooled, 800 ml of water are added, and the mixture is extracted with 2×500 ml of ethyl acetate. The organic phases are combined and washed with 300 ml of water, and the solvent is removed at 30° under reduced pressure. The dark-orange oil which remains (9.7 g) is purified by chromatography (300 g of silica gel; MTB ether/heptane 5:1; 1.5 litres). 9.9 g of pale-yellow crystals remain (67%), m.p. 101–103°; MS 296 (M+), 205, 119, 91 (100%).

2) Synthesis of ethyl 4-(4-benzylpiperazin-1-yl)-2-formylphenoxyacetate

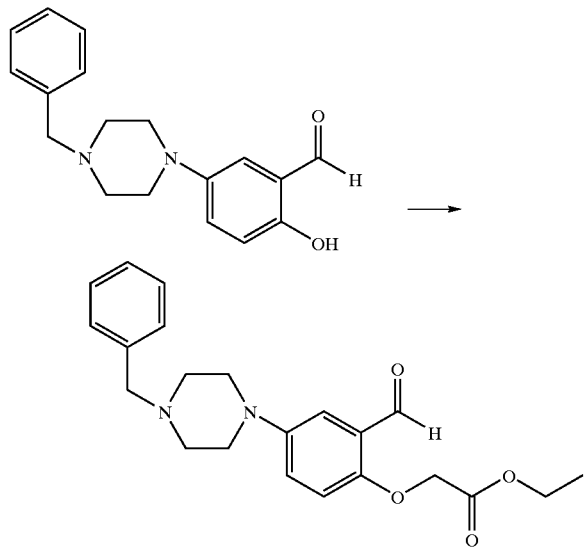

0.5 g of 5-(4-benzylpiperazin-1-yl)-2-hydroxybenzaldehyde are dissolved in 5 ml of NMP at 20° C. under nitrogen with stirring, and 0.25 g of potassium carbonate and 0.2 ml of ethyl bromoacetate are added. The mixture is stirred at 110° for 4 hours and cooled to 15°. 30 ml of water and 30 ml of ethyl acetate are added to the mixture, the phases are separated, and the aqueous phase is extracted with 30 ml of ethyl acetate. Combined organic phases are washed with 2×30 ml of water and freed from solvent under reduced pressure. The yellow oil which remains (0.7 g) is chromatographed on 10 g of silica gel (MTB ether/heptane 5:1) and gives 0.45 g of product (70%; yellowish oil), MS 382 (M+), 296, 263, 199, 149, 119, 91 (100%).

EXAMPLE 5

1) Synthesis of ethyl 5-(4-benzylpiperazin-1-yl)benzofuran-2-carboxylate

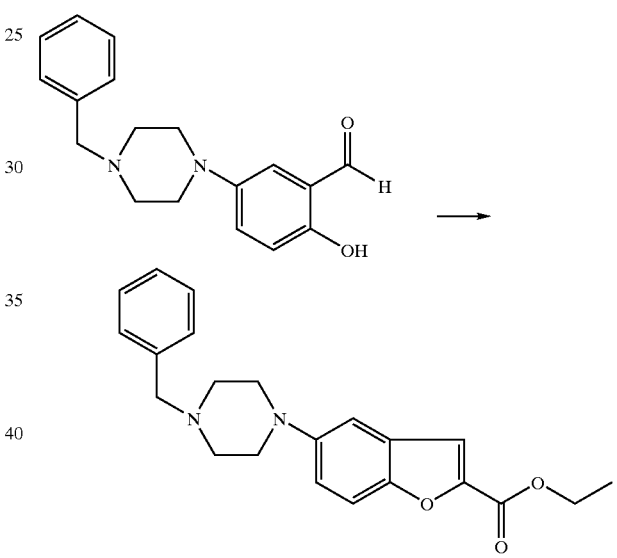

0.5 g of 5-(4-benzylpiperazin-1-yl)-2-hydroxybenzaldehyde is added at 20° with stirring to 5 ml of NMP, and 0.25 g of potassium carbonate and 0.2 ml of ethyl bromoacetate are added to the solution. The mixture is stirred at 105° for 15 hours and then cooled to 25°. The batch is added to 30 ml of water (10°) with stirring, the aqueous phase is extracted at 10° with 3×50 ml of ethyl acetate, and the combined organic phases are washed with 50 ml of water and then freed from solvent under reduced pressure (1.2 g of orange oil). Column chromatography on 30 g of silica gel (MTB ether/heptane 5:1) gives 0.43 g of pale-yellow crystals (71%), m.p. 105–107°; MS 364 (M+), 268, 204, 146, 119, 91 (100%).

A sample of the corresponding hydrochloride (m.p. 219–222°) can be obtained by dissolution in ethanol, addition of aqueous 1N hydrochloric acid, isolation of the resultant solid and drying under reduced pressure.

EXAMPLE 6

1) Synthesis of 5-(4-benzylpiperazin-1-yl)benzofuran-2-carboxamide

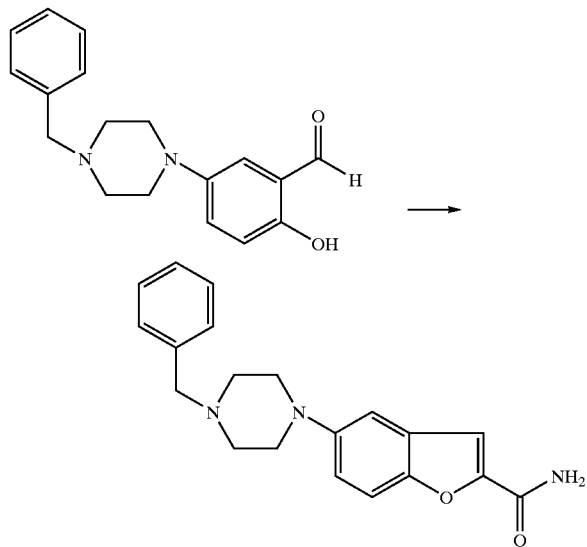

500 mg of 5-(4-benzylpiperazin-1-yl)-2-hydroxybenzaldehyde are added at 20° under nitrogen with stirring to 5 ml of NMP, and 0.25 g of potassium carbonate and 0.2 ml of ethyl bromoacetate are added to the solution. The mixture is stirred at 105° for 15 hours and cooled to 25°. 0.2 ml of formamide is then added to the mixture, and stirring is continued for 30 minutes. 1 ml of sodium methoxide (30% solution in methanol) is then added at 25° over the course of 15 minutes, and the mixture is stirred at 25–30° for a further 3 hours. The reaction mixture is poured into 30 ml of water (10°), the aqueous phase is extracted at 10° with 3×50 ml of ethyl acetate, the combined organic phases are washed with 50 ml of water, and the solvent is removed under reduced pressure (0.7 g of orange oil). The oil is recrystallized from 10 ml of toluene (375 mg of pale-yellow crystals; 66%), m.p. 206–208°; MS 335 (M+), 244, 189, 146, 91 (100%).

Removal of the protecting group gives 5-(1-piperazinyl)benzofuran-2-carboxamide.

EXAMPLE 7

1) Synthesis of 5-(4-tert-butoxycarbonylpiperazin-1-yl)-2-hydroxybenzaldehyde

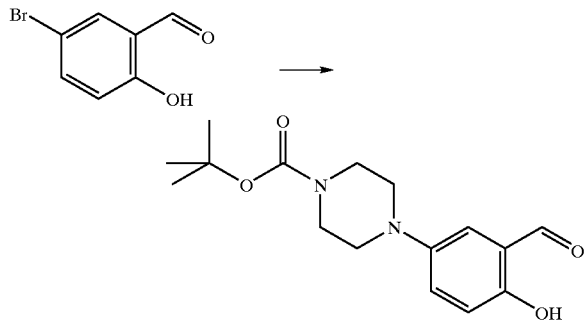

0.58 g of bis(dibenzylideneacetone)palladium and 0.16 g of tri-tert-butylphosphine are added under nitrogen to 200 ml of toluene, and the resultant solution, which becomes dark red, is stirred at 20° for 30 minutes. 10 g of 5-bromo-2-hydroxybenzaldehyde, 10.2 g of tert-butyl 1-piperazinecarboxylate and 7.2 g of sodium tert-butoxide are then added. The mixture is stirred at 60° for 24 hours and cooled, 800 ml of water are added, and the mixture is extracted with 2×500 ml of ethyl acetate. The organic phases are combined and washed with 300 ml of water, and the solvent is removed at 30° under reduced pressure. The dark-orange oil which remains (11 g) is purified by chromatography (300 g of silica gel; MTB ether/heptane 5:1; 1.5 litres) leaving 7.8 g of pale-yellow crystals (51%), m.p. 84–86°; MS 306 (M+), 250 (100%), 233, 176, 164.

2) Synthesis of ethyl 4-(4-tert-butoxycarbonylpiperazin-1-yl)-2-formylphenoxyacetate

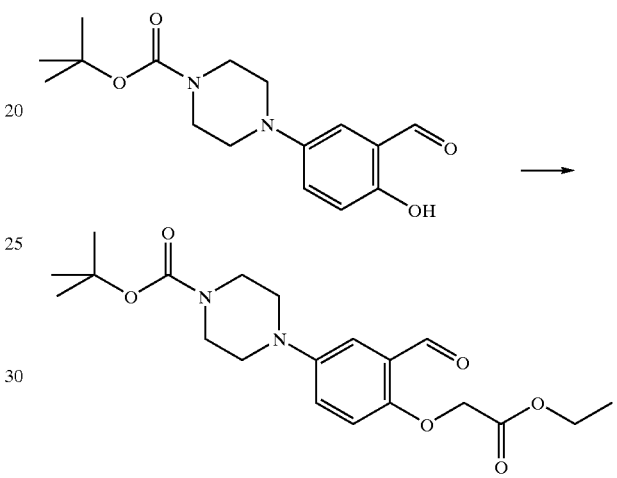

0.5 g of 5-(4-tert-butoxypiperazin-1-yl)-2-hydroxybenzaldehyde are dissolved in 5 ml of NMP at 20° under nitrogen with stirring, and 0.25 g of potassium carbonate and 0.2 ml of ethyl bromoacetate are added. The mixture is stirred at 110° for 30 minutes and cooled to 25°. 30 ml of water and 30 ml of ethyl acetate are added to the mixture, the phases are separated, and the aqueous phase is extracted with 30 ml of ethyl acetate. The combined organic phases are washed with 30 ml of water and freed from solvent under reduced pressure. 30 ml of toluene, 30 ml of water and 5 ml of 1N HCl are added to the crystal slurry which remains, the toluene phase is removed under reduced pressure, and the crystalline precipitate is separated off and dried at 40° under reduced pressure (0.48 g; 75%), m.p. 93–94° C.; MS 392 (M+), 336 (100%), 250/249, 57.

EXAMPLE 8

1) Synthesis of ethyl 5-(4-tert-butoxycarbonylpiperazin-1-yl)benzofuran-2-carboxylate

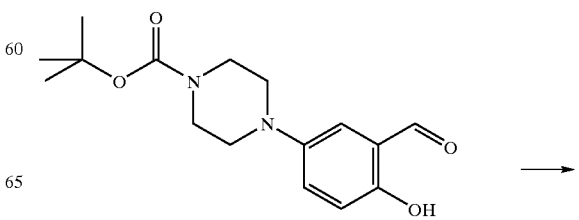

-continued

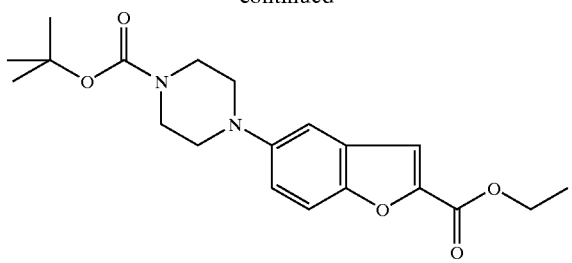

520 mg of 5-(4-tert-butoxycarbonylpiperazin-1-yl)-2-hydroxybenzaldehyde are added at 20° under nitrogen with stirring to 5 ml of NMP, and 0.25 g of potassium carbonate and 0.2 ml of ethyl bromoacetate are added to the solution. The mixture is stirred at 105° for 3 hours and then cooled to 25°. The batch is added to 30 ml of water (10°) with stirring, the aqueous phase is extracted at 10° with 3 times 30 ml of ethyl acetate, and the combined organic phases are washed with 30 ml of saturated NaCl solution and with 30 ml of water and then freed from solvent under reduced pressure (0.6 g of orange oil with crystal components). After chromatography on 30 g of silica gel (MTB ether/heptane 5:1), 0.45 g of pale-yellow crystals can be isolated (70%), m.p. 116–117°; MS 374 (M+), 318 (100%), 244, 232.

EXAMPLE 9

1) Synthesis of 5-(4-tert-butoxycarbonylpiperazin-1-yl)benzofuran-2-carboxamide

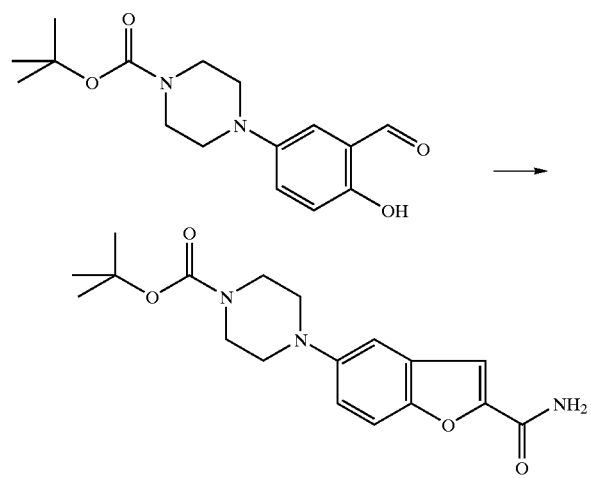

1.04 g of 5-(4-tert-butoxycarbonylpiperazin-1-yl)-2-hydroxybenzaldehyde are added at 20° under nitrogen with stirring to 10 ml of NMP, and 0.5 g of potassium carbonate and 0.4 ml of ethyl bromoacetate are added to the solution. The mixture is stirred at 120° for 5 hours and cooled to 25°. 0.4 ml of formamide is then added to the mixture, and stirring is continued for 30 minutes. 1.9 ml of sodium methoxide (30% solution in methanol) are then added over the course of 15 minutes without cooling, and stirring is continued for a further hour at 25–30°. 30 ml of water and 30 ml of ethyl acetate are added to the batch, the phases are separated, and the aqueous phase is extracted with 30 ml of ethyl acetate. The combined organic phases are washed with 30 ml of water, and the solvent is removed under reduced pressure (1.1 g of orange crystal slurry). After crystallization using 20 ml of toluene, 500 mg of pale-beige crystals remain. The mother liquor is evaporated, and the oil which remains is dissolved in 10 ml of toluene. After 3 hours at 0°, further pale-beige crystals form (identical with the first crystals; 70 mg). The total yield (0.57 g) is 49%, m.p. 202–204°; MS 345 (M+), 289 (100%), 272, 244, 215, 203.

The BOC group is removed as described, giving 5-(1-piperazinyl)benzofuran-2-carboxamide.

EXAMPLE 10

1) Synthesis of 5-(4-tert-butoxycarbonylpiperazin-1-yl)benzofuran-2-carboxamide 5 ml of 1-methyl-2-pyrrolidone, 0.16 g of chloroacetamide and 0.25 g of potassium carbonate are added at 20° C. with stirring/under nitrogen to 0.5 g of 5-(4-tert-butoxycarbonylpiperazin-1-yl)-2-hydroxybenzaldehyde. The mixture is stirred at 60° C. for 16 hours, cooled and then filtered, and the solvent is removed under reduced pressure. The residue is taken up in MTB ether, re-filtered and concentrated, and the residue is crystallized from toluene. The isolated yield is 0.34 g (60%).

2) Synthesis of 5-(4-benzylpiperazin-1-yl)benzofuran-2-carboxamide 10 ml of 1-methyl-2-pyrrolidone, 0.4 g of chloroacetamide and 0.8 g of potassium carbonate are added at 20° C. with stirring/under nitrogen to 1.0 g of 5-(4-benzylpiperazin-1-yl)-2-hydroxybenzaldehyde. The mixture is stirred at 60° C. for 16 hours, cooled and then filtered, and the solvent is removed under reduced pressure. The residue is taken up in MTB ether, re-filtered and concentrated, and the residue is crystallized from toluene. The isolated yield is 0.73 g (65%).

What is claimed is:

1. A process for the preparation of 5-(1-piperazinyl)benzofuran-2-carboxamide, comprising a) 5-bromosalicylaldehyde is reacted in a one-pot reaction firstly with a compound of the formula I $$L-CH_2-COOR^1 \qquad I$$

in which

L is Cl, Br or I or a reactively esterified OH group, and $R^1$ is alkyl having 1–6 carbon atoms or benzyl, and subsequently with formamide to give 5-L-benzofuran-2-carboxamide, in which L is Cl, Br or I or a reactively esterified OH group, the 5-L-benzofuran-2-carboxamide is then reacted in a transition metal-catalysed amination with $R^2$-piperazine, in which $R^2$ is H or an amino protecting group, to give the compound of the formula III

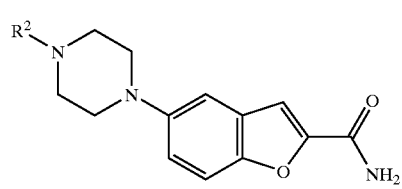

III in which R² is H or an amino protecting group,
and subsequently, if R²≠H, R² is cleaved off, or
b) a compound of the formula IV

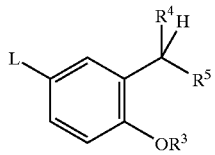

IV in which
L is Cl, Br, I or a reactively esterified OH group,
R³ is H or CH₂R⁶,
R⁴ and R⁵ are each, independently of one another, OR⁷, OR⁸, SR⁷ or SR⁸,
R⁴ and R⁵ together are alternatively carbonyl, =S, =N—C(R⁷)₂, =N—C(R⁸)₂, =N—OH, =N—OR⁷, =N—N[(R⁷)₂], =N—N[(R⁸)₂] or —O—(CH₂)ₙ—O—,
R⁶ is CN, COOH, COOR⁷ or CONH₂,
R⁷ is alkyl having 1–6 carbon atoms,
R⁸ is phenyl which is unsubstituted or mono- or disubstituted by R⁷, OR⁷, SR⁷ or Hal,
n is 2 or 3,
is reacted in a transition metal-catalysed amination with R²-piperazine, in which R² is H or an amino protecting group,
to give a compound of the formula V

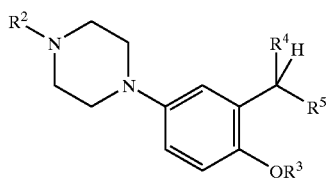

V in which
R² is H or an amino protecting group,
R³ is H or CH₂R⁶,
R⁴ and R⁵ are each, independently of one another, OR⁷, OR⁸, SR⁷ or SR⁸,
R⁴ and R⁵ together are alternatively carbonyl, =S, =N—C(R⁷)₂, =N—C(R⁸)₂, =N—OH, =N—OR⁷, =N—N[(R⁷)₂], =N—N[(R⁸)₂] or —O—(CH₂)ₙ—O—,
R⁶ is CN, COOH, COOR⁷ or CONH₂,
R⁷ is alkyl having 1–6 carbon atoms,
R⁸ is phenyl which is unsubstituted or mono- or disubstituted by R⁷, OR⁷, SR⁷ or Hal,
n is 2 or 3,
which is subsequently reacted in a one-pot reaction firstly with a compound of the formula I

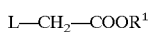

L—CH₂—COOR¹    I in which
L is Cl, Br, I or a reactively esterified OH group, and
R¹ is alkyl having 1–6 carbon atoms or benzyl,
and subsequently with formamide to give a compound of the formula III

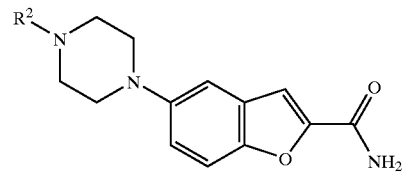

III in which R² is H or an amino protecting group,
and subsequently, if R²≠H, R² is cleaved off, or
c) a compound of the formula V as illustrated above,
in which
R² is an amino protecting group,
R³ is H or CH₂R⁶,
R⁴ and R⁵ are each, independently of one another, OR⁷, OR⁸, SR⁷ or SR⁸,
R⁴ and R⁵ together are alternatively carbonyl, =S, =N—C(R⁷)₂, =N—C(R⁸)₂, =N—OH, =N—OR⁷, =N—N[(R⁷)₂], =N—N[(R⁸)₂] or —O—(CH₂)ₙ—O—,
R⁶ is CN, COOH, COOR⁷ or CONH₂,
R⁷ is alkyl having 1–6 carbon atoms,
R⁸ is phenyl which is unsubstituted or mono- or disubstituted by R⁷, OR⁷, SR⁷ or Hal,
n is 2 or 3,
is reacted with chloroacetamide to give a compound of the formula III as illustrated above,
in which
R² is an amino protecting group,
and R² is subsequently cleaved off,
or optionally 5-(1-piperazinyl-)benzofuran-2-carboxamide is converted into one of its acid-addition salts by treatment with an acid.

2. A process according to claim 1, wherein Hal is Br.

3. A process according to claim 1, wherein Pd(OAc)₂/P(tert-butyl)₃ is used during the transition metal-catalyzed amination.

4. A process according to claim 1, wherein in the reaction of 5-bromosalicylaldehyde or a compound of the formula V with a compound of the formula I, a solvent is used which is N-methylpyrrolidone.

5. A compound of the formula V

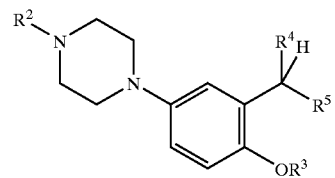

V in which
R² is H or an amino protecting group,
R³ is H or CH₂R⁶,
R⁴ and R⁵ are each, independently of one another, OR⁷, OR⁸, SR⁷ or SR⁸,
R⁴ and R⁵ together are alternatively carbonyl, =S, =N—C(R⁷)₂, =N—C(R⁸)₂, =N—OH, =N—OR⁷, =N—N[(R⁷)₂], =N—N[(R⁸)₂] or —O—(CH₂)ₙ—O—,
R⁶ is CN, COOH, COOR⁷ or CONH₂, $R^7$ is alkyl having 1–6 carbon atoms, $R^8$ is phenyl which is unsubstituted or mono- or disubstituted by $R^7$, $OR^7$, $SR^7$ or Hal, and n is 2 or 3, or a salt or solvate thereof.

6. A process according to claim 1, wherein L is Cl or Br.

7. A process according to claim 1, wherein $R^2$ is an amino protecting group.

8. A process according to claim 1, wherein $R^2$ is benzyl or BOC.

9. A process according to claim 1, wherein $R^3$ is H.

10. A process according to claim 1, wherein $R^4$ and $R^5$ are, each independently, methoxy, ethoxy, propoxy or phenoxy, or together carbonyl.

11. A process according to claim 1, wherein

=N-C($R^7$)$_2$ is =N-C(CH$_3$)$_2$,

=N-C($R^8$)$_2$ is =N-C(phenyl)$_2$,

=N-O$R^7$ is =N-OCH$_3$,

=N-N[($R^7$)$_2$]is =N-N[(CH$_3$)$_2$], and

=N-N[($R^8$)$_2$]is =N-N[(phenyl)$_2$].

12. A compound according to claim 5, wherein $R^2$ is an amino protecting group.

13. A compound according to claim 5, wherein $R^2$ is benzyl or BOC.

14. A compound according to claim 5, wherein $R^3$ is H.

15. A compound according to claim 5, wherein $R^4$ and $R^5$ are, each independently, methoxy, ethoxy, propoxy or phenoxy, or together carbonyl.

16. A compound according to claim 5, wherein

=N-C($R^7$)$_2$ is =N-C(CH$_3$)$_2$,

=N-C($R^8$)$_2$ is =N-C(phenyl)$_2$,

=N-O$R^7$ is =N-OCH$_3$,

=N-N[($R^7$)$_2$] is =N-N[(CH$_3$)$_2$], and

=N-N[($R^8$)$_2$] is =N-N[(phenyl)$_2$].

* * * * *

UNITED STATES PATENT AND TRADEMARK OFFICE
CERTIFICATE OF CORRECTION

PATENT NO. : 6,762,300 B2
DATED : July 13, 2004
INVENTOR(S) : Andreas Bathe et al.

It is certified that error appears in the above-identified patent and that said Letters Patent is hereby corrected as shown below:

Column 17,
Line 38, the formula should read:

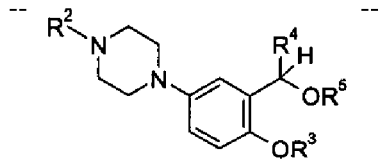

Column 18,
Line 36, reads "piperazinyl-)" should read -- piperazinyl) --.
Line 53, the formula should read:

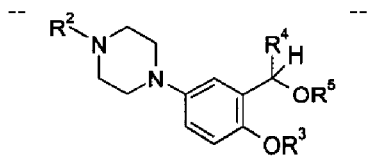

Column 20,
Line 1, "=N-N[($R^7$)$_2$]is" should read -- =N-N[($R^7$)$_2$] is --.
Line 2, "=N-N[($R^8$)$_2$]is" should read -- =N-N[($R^7$)$_2$] is --.

Signed and Sealed this

Twenty-second Day of March, 2005

JON W. DUDAS
*Director of the United States Patent and Trademark Office*